United States Patent [19]
Gottenauer et al.

[11] Patent Number: 5,881,719
[45] Date of Patent: Mar. 16, 1999

[54] INHALER FOR ADMINISTERING MEDICAMENTS FROM BLISTER PACKS

[75] Inventors: Wolfgang Gottenauer, Bruchkobel; Andre Narodylo, Linsengericht; Joachim Goede, Hanau, all of Germany

[73] Assignee: ASTA Medica Aktiengesellschaft, Dresden, Germany

[21] Appl. No.: 671,739

[22] Filed: Jun. 28, 1996

[30] Foreign Application Priority Data

Jun. 30, 1995 [DE] Germany ................. 195 23 516.9

[51] Int. Cl.⁶ ................................................ A61M 16/00
[52] U.S. Cl. .............................. 128/203.15; 128/203.12; 128/203.21; 604/58
[58] Field of Search .................. 128/203.15, 203.21, 128/203.23, 203.12, 203.18, 203.19, 203.24; 604/57, 58; 206/531, 532, 222

[56] References Cited

U.S. PATENT DOCUMENTS

| | | | |
|---|---|---|---|
| 3,054,503 | 9/1962 | Hartman et al. | 206/42 |
| 3,669,113 | 6/1972 | Altounyan et al. | 128/266 |
| 4,015,717 | 4/1977 | Richardson et al. | 206/534 |
| 4,074,806 | 2/1978 | Ardito | 206/531 |
| 4,953,545 | 9/1990 | McCarty | 128/200.14 |
| 5,301,666 | 4/1994 | Lerk et al. | 128/203.15 |
| 5,337,740 | 8/1994 | Armstrong et al. | 128/203.15 |
| 5,349,947 | 9/1994 | Newhouse et al. | 128/203.21 |
| 5,492,112 | 2/1996 | Mecikalski | 128/203.15 |
| 5,507,281 | 4/1996 | Kuhnel et al. | 128/203.15 |

FOREIGN PATENT DOCUMENTS

| | | | |
|---|---|---|---|
| 0645056 | 9/1991 | Australia | A61M 15/00 |
| 0 315 951 A1 | 4/1983 | European Pat. Off. . | |
| 0 211 595 | 2/1987 | European Pat. Off. | A61M 15/00 |
| 0469814 | 7/1991 | European Pat. Off. . | |
| 0 469 814 A1 | 2/1992 | European Pat. Off. . | |
| 0528764 | 2/1993 | European Pat. Off. | A61M 15/00 |
| 2010520 | 2/1970 | France | A61M 15/00 |
| 1 262 085 | 6/1968 | United Kingdom . | |
| 2129691 | 5/1984 | United Kingdom | A61M 15/00 |
| 2 142 246 | 1/1985 | United Kingdom . | |
| 2142246 | 1/1985 | United Kingdom | A61M 15/00 |
| 2253200 | 9/1992 | United Kingdom | 128/203.12 |
| 2 270 293 | 3/1994 | United Kingdom . | |
| 2270293 | 3/1994 | United Kingdom . | |
| WO 94/08552 | 4/1994 | WIPO . | |

OTHER PUBLICATIONS

International Search Report Dated Oct. 30, 1996.

*Primary Examiner*—John G. Weiss
*Assistant Examiner*—Virendra Srivastava
*Attorney, Agent, or Firm*—Baker & Daniels

[57] ABSTRACT

The present invention relates to an inhaler for administering medicaments (38) from blister packs (5), which has a housing with a mouthpiece (1) on one side, an air inlet opening (32) on the opposite side and, between them on the inside, a duct (7) which connects the mouthpiece (1) and the air inlet opening (32), it being possible for at least one blister strip (5) to be inserted into the housing so that the covering foil (35) of the inserted blister strip (5) adjoins the duct (7). The housing has means for pressing out the individual cavities (31) of the blister strip (5), which means contain at least one plunger (10) with a curved plunger surface, which corresponds to the shape of the blister cavities (31), for engagement on the blister cavity.

11 Claims, 7 Drawing Sheets

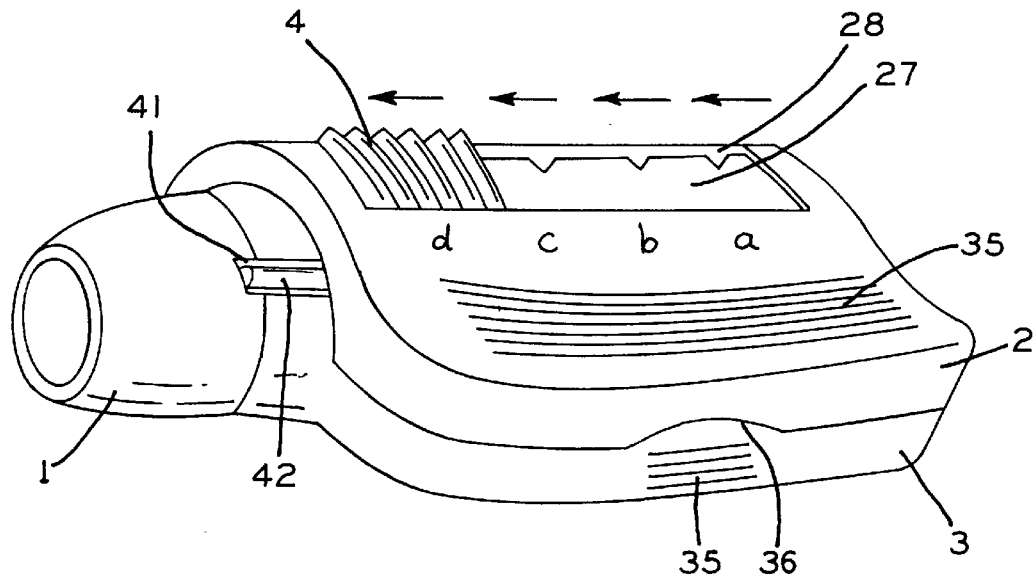
FIG_1
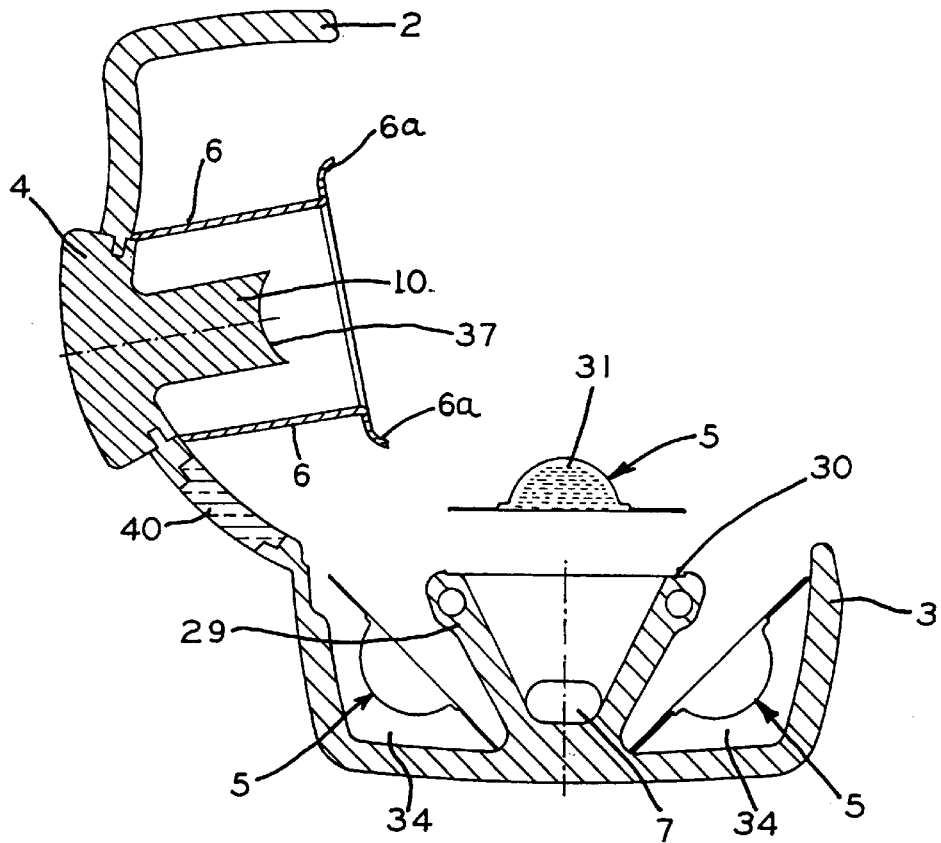
FIG_2

FIG_8

INHALER FOR ADMINISTERING MEDICAMENTS FROM BLISTER PACKS

BACKGROUND OF THE INVENTION

The invention relates to an inhaler for administering medicaments from blister packs, in which the blister cavities are emptied by means of a pressing-out aid.

Inhalers for administering medicaments to patients in a solid form distributed finely in an air flow, so-called powder inhalers, are used nowadays in great numbers and many embodiments in inhalation therapy. They partially replace the previously customary suspension inhalers, in which the aerosol is produced by means of a halogenated hydrocarbon as propellent gas, and whose use is no longer desirable for reasons of environmental protection. Most of the previously known powder inhalers use a device of a technically relatively complex design, with which a patient gives himself inhalable powder portions (doses) by inhalation.

One possibility of predosing medicaments is the packaging of appropriate portions in so-called "blister packs", which are also used, for example, for packaging tablets with the possibility of hygienic individual removal. EP-B-211 595, GB-A-2,129,691 and GB-A-2,142,246 disclose powder inhalers which release the medicament from blister packs in which it is enclosed in a solid, finely distributed form. A disc-shaped blister pack is inserted into the powder inhalers described in EP-B-211,595 and GB-A-2,129,691, the powder portion is released by a plunger when the inhaler is used, and the blister disc is replaced by a new one when it has been completely emptied. GB-A-2,142,246 relates to an inhaler into which a blister pack comprising a single chamber is inserted and is opened for use with a kind of mandrel.

An inhaler which is easy to handle and is inexpensive is described in the subsequently published DE-A-44 00 084. The inhaler comprises a housing which forms an elongate interior, is sealed off relative to the outside, and has a mouthpiece on a narrow side and an air inlet opening on the opposite side, regions with blister cavities being arranged at least on one main surface of the housing. In one embodiment, the housing comprises an open structure into which one or more strips can be introduced, for example by pushing them or inserting them into a structure which can be pivoted open. In all these embodiments of the inhalers, the user has to press the individual cavities of the blister pack open with his fingers, i.e. exert pressure on the outwardly curved dome so that the thin covering foil tears open and the medicament can drop into the interior of the housing. The disadvantage with these inhalers is that the powder in the blister cavities is mechanically loaded and compressed when the latter are pressed open by the finger, and thus can no longer be finely distributed, or can only be insufficiently distributed, in the inhalation flow.

All these powder inhalers have the disadvantage that they are extremely cumbersome, i.e. the device volume is relatively large in relation to the proportioned dose quantity used. Depending on the volume and number of parts per device, carrying a known powder inhaler can be inconvenient for the patient. Moreover, with the different, often complicated functioning principles, there is the risk that the devices may not be handled properly, or possibly cannot be handled at all, in an emergency (e.g. in an acute asthma attack) or in the case of little technical understanding on the part of the patient.

SUMMARY OF THE INVENTION

The present invention is therefore based on the problem of providing a handy, easy-to-operate powder inhaler for use with blister packs, in which inhaler the compression of the medicament in the blister cavities is avoided during the pressing-out operation so that the medicament can be finely dispersed in the inhalation flow.

This object is achieved by an inhaler for administering medicaments from strip-shaped blister packs, which has a housing with a mouthpiece on one side, an air inlet opening on the opposite side and, between them, a duct and a receiving bearing for a blister strip to be inserted in such a way that the covering foil of the inserted blister strip, which seals the cavities containing the medicament, adjoins the duct, characterized in that the housing has means for pressing out the individual cavities of the blister strip, and these means have at least one plunger with a curved plunger surface which corresponds to the shape of the convex blister cavities.

Preferred embodiments of the invention are described in the subclaims.

The inhaler according to the invention serves to administer medicaments from blister packs. Blister packs are packs which comprise a container film with small, filled depressions or cavities and a covering foil which seals the depressions. In this case, the term "blister pack" is to be understood within the scope of the present invention in the widest sense for packs of this type, irrespective of the type of container film or its method of manufacture. The container film has such a wall thickness in the region of the cavities that it is possible to press the cavity in from the outside, and the covering foil tears open as a result of the pressing-in. The operation of pressing the cavity in from the outside with simultaneous tearing-open of the covering foil and release of the medicament is described in the following as "pressing-out".

The housing of the inhaler according to the invention preferably has an elongate shape with the mouthpiece on one narrow side and the air inlet opening on the opposite narrow side. The blister strip which is inserted into the housing has a row of cavities arranged one after the other. The inhaler is designed in such a way that it can only ever receive blister strips with a particular number of cavities, the number of cavities depending on the type and dosage of the medicament to be administered. An inhaler which is suitable for many applications is designed for the use of blister strips with four cavities.

A preferred embodiment of the inhaler has a housing which can be pivoted open and comprises at least two housing parts which are pivotably connected to one another via a joint or hinges. The housing can, for example, have a bottom part and an upper part, which parts are pivotably connected to one another, or it can even have an additional central part. In the bottom part or central part of the housing, there is a receiving bearing with a recess for receiving the blister strip. The upper part of the housing may additionally have inwardly directed webs for pressing the blister strip against the receiving bearing in order to fix the blister strip in the closed inhaler.

The pressing-out means of the inhaler according to the invention have at least one plunger with a curved plunger surface adapted to the shape of the blister cavities. Since the customary blister packs have cavities whose curvature has the shape of a spherical cap from the outside, the curvature of the engaging plunger surface is usually designed to be complementary to a spherical cap. The concave curvature of the engaging plunger surface adapted to the convexly curved shape of the blister cavities prevents the medicament from being compressed inside the cavities when they are pressed out and thus from no longer being able to be dispersed sufficiently in the air flow.

The pressing-out means are advantageously integrated in the housing. In order to open and to empty a blister cavity with the aid of the pressing-out means, the user has to press parts of the pressing-out means or the entire pressing-out means with his fingers or whole hand. In this case, the transmission of force to the plunger of the pressing-out means, whose surface engages on the outwardly curved blister cavity, can take place directly or by means of a lever transmission. In the case of means with leverage, these can be designed in the form of a plurality of individual levers, each having a pressing-out plunger, or as one lever with a displaceable, engaging pressing-out plunger.

In a preferred embodiment of the invention, the pressing-out means are integrated in the upper part of the housing and act without a lever transmission. Particularly advantageous is a constructional design of the pressing-out means with four pressing-out plungers which are mounted in the upper part of the housing by means of grip plates and, when required, are pressed down by the user one after the other in order to empty the blister cavities.

In another preferred embodiment of the invention, the upper part of the housing itself forms the pressing-out means. Particularly advantageous is the design of the upper part of the housing as a single lever with a displaceable, engaging pressing-out plunger. As an alternative thereto, the upper part of the housing can also be formed from a plurality of single levers which are pressed down one after the other for use.

The pressure due to the plunger surface on the cavity causes the thin covering foil of the blister pack to tear open and the medicament either still to remain in the cavity due to adherence forces or to drop directly into the powder duct of the housing.

During inhalation by sucking on the mouthpiece of the inhaler, the user generates a slight negative pressure in the air duct, which causes the medicament still remaining in the cavity to be conveyed into the duct and air to enter the duct through the air inlet opening. Moreover, since the air flow in the duct generates a partial negative pressure when flowing past the opened cavity (injection effect), the medicament is to a great extent sucked out of the cavity without leaving a residue. The air flow then exits from the inhaler via the mouthpiece, carrying the medicament along with it, and is inhaled by the user so that the medicament can pass into the lung.

For reasons of favourable air conduction in the air duct, it is advantageous to tear open or sever the covering foil of the blister pack in a defined manner. It is therefore desirable for the part of the covering foil which originally sealed the cavity to project into the interior of the duct after opening as a kind of tag which is attached at only one point, the intention being for the tag to be aligned parallel to the air flow. This is achieved, for example, by using specially designed blister packs. For instance, the individual cavity may be partially surrounded by an annular bead, as a result of which the covering foil is severed, during pressing-out, in the region of the bead and, in the region in which the bead is interrupted, remains connected to the remaining covering foil; or the covering foil is provided with predetermined tearing points. The asymmetrical design of the cavities, for example in a shape which is chamfered on one side, likewise leads to a defined tearing-open of the covering foil.

In order to achieve defined tearing-open of the covering foil when using customary blister packs, the plunger must engage asymmetrically on the blister cavity during the pressing-out operation. This is achieved, for example, by the pressing-out plunger itself having an asymmetrical cross-section, i.e. the edge of the curved plunger surface extends in a plane which, at an angle not equal to 90° relative to the longitudinal axis of the plunger, intersects a perpendicular plane extending in the longitudinal direction of the housing, so that the plunger engages firstly on one side of the outwardly curved blister cavity when it is pressed down. The covering foil then tears open firstly in this contact region, while it remains connected to the remaining covering foil on the opposite side of the cavity. A likewise asymmetrical engagement of the plunger on the blister cavity is achieved in a symmetrically designed pressing-out plunger if the latter is connected to the housing laterally by means of a lever arm in such a way that the plunger, when it is pressed down by the user, carries out a movement along an arc about the pivot of the housing part, and that the engagement on the blister cavity firstly takes place on one side. The pressing-out plunger of asymmetrical cross-section in the longitudinal direction can also be combined with the lever arrangement. Of course, the blister packs with asymmetrical cavities described above can also be used in an inhaler in which the pressing-out device engages asymmetrically on the blister cavity.

Preferred embodiments of the inhaler according to the invention have a mouthpiece, in whose interior a cyclone chamber with tangential air inlet slots is arranged, into which secondary air can enter through an appropriate duct. When, after opening a blister cavity, the user sucks on the mouthpiece, the medicament passes via the duct to the mouthpiece where, due to the cyclone effect, it is dispersed with tangentially inflowing secondary air and is thus rendered more readily inhalable. This secondary air, sucked in to assist the powder dispersion, preferably amounts to about 75% of the total air flow. This means that about 25% of the total air flow is conducted through the duct. On account of this air flow, the medicament is conveyed from the cavity through the air duct, through a corresponding opening, perpendicularly onto a deflector and then tangentially through a further opening into the cyclone chamber.

In order to prevent the medicament dropping out through the air inlet opening after a blister cavity has been pressed out, due to the inhaler being held vertically, the space directly behind the opening can be provided with built-in webs which deflect the air path and extend it in the form of a labyrinth. In order furthermore to avoid the medicament being carried out of the inhaler by air being blown into the mouthpiece, the air inlet opening for the powder duct is preferably provided with a non-return valve which opens under a slight negative pressure in the interior of the housing and closes under normal or overpressure in the housing interior. A suitable non-return valve is a diaphragm valve in which a diaphragm is arranged on the inner side of the housing, which diaphragm covers the inlet opening and is placed against the end face, under overpressure in the housing, and closes the inlet opening. Spring-loaded ball valves or other non-return valves can also be used for closing the air inlet opening.

The housing of the inhaler according to the invention can have one or more additional recesses or chambers to receive one or more replacement blister packs.

The inhaler is preferably made of plastic; suitable materials are, for example, thermoplastics, such as polyoxymethylene (polyacetal), polycarbonate, polymethylmethacrylate, polypropylene, polyethylene, polyvinyl chloride and acrylonitrile-butadiene-styrene copolymer (ABS), singly or in combination. Elastomeric polymers with spring-elastic characteristics are suitable for the design of the webs for fixing the blister strip.

Blister packs made of various materials can be used in the inhaler of the present invention. The material of the container film is preferably a thermo-formable polymer, such as polypropylene, polyethylene, polyvinyl chloride, polystyrene, or a metal which can be deep-drawn, such as aluminium, also with a laminated polymer. Other thermo-formable materials customary for blister packs are also suitable. Such shaped parts with depressions produced by thermoforming have an even wall thickness of the container film both over the areas of the depressions and over the other areas. However, an injection-mouldable material or another mouldable material or a material which can be processed by blow-moulding, for example an elastomeric material, can also be used, for example, as material for the container film, and the shaped part with the depressions can correspondingly be produced by injection-moulding or another moulding method or by blow-moulding. In this case, the wall thickness of the container film can be varied optionally in various areas. The covering foil is preferably made of metal, for example aluminium, or aluminium alloys, with a laminated polymer. Other materials, including those which are customary and known for blister packs, can also be used. The covering foil can be connected to the container film in various ways, for example by welding or bonding as is customary. In the inhaler according to the invention, it is also possible to use blister packs in which the individual cavities are surrounded by an annular bead moulded out of the container film. These blister packs have the advantage of additionally reducing the mechanical loading on the medicament during pressing-out.

A powder inhaler for use with blister packs is provided by the present invention, which inhaler is easy to operate and provides the medicament to the user in a sufficiently dispersed and thus inhalable form.

BRIEF DESCRIPTION OF THE INVENTION

The invention will be explained with reference to different embodiments illustrated in the following figures.

FIG. 1 shows, in a perspective illustration, an inhaler with a pressing-out means designed as a single lever.

FIG. 2 shows a cross-section of the inhaler illustrated in FIG. 1 with the housing pivoted open and a blister cavity in cross-section.

DESCRIPTION OF THE PREFERRED EMBODIMENT

Figure 3:
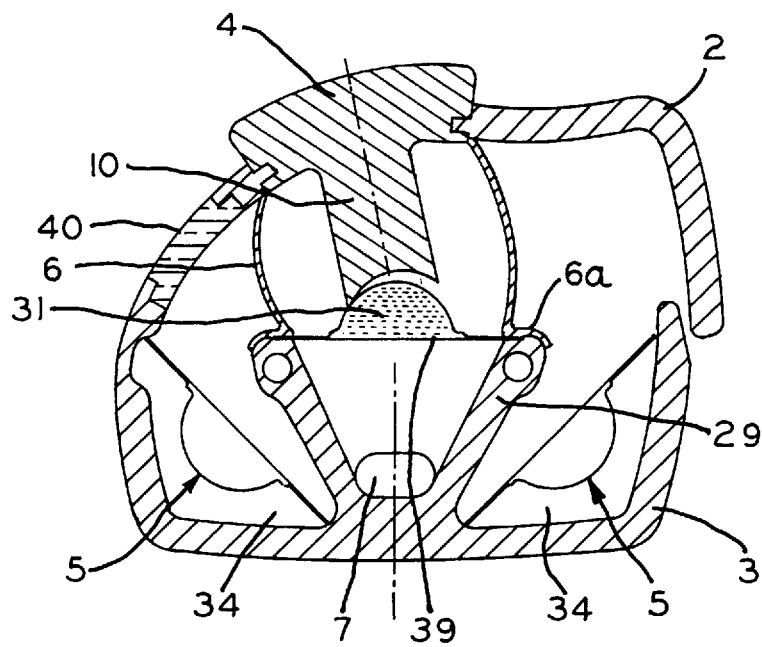
FIG. 3 shows a cross-section of the inhaler illustrated in FIG. 1 with the housing pivoted closed and a blister cavity inserted.

All the inhalers illustrated are for the use of blister strips with four successively arranged cavities which are emptied successively by the user and whose content is inhaled.

In the embodiment of the present invention illustrated in FIG. 1, the pressing-out device is designed as a single lever 2 which constitutes the upper part 2 of the housing at the same time. The upper part 2 of the housing is connected to the bottom part 3 of the housing by means of a film hinge, the upper part 2 of the housing engaging slightly beyond the bottom part 3 of the housing in the fitted-together state. A mouthpiece 1, shaped essentially like a truncated cone, is attached to the narrow side of the bottom part 3 of the housing. Located in the single lever 2 is a rectangular recess 27 in which the approximately square grip plate 4 of the pressing-out plunger 10 engages (not visible in FIG. 1). The grip plate 4 is displaceable in the recess 27, it being possible for the said grip plate to be fixed in an engaging manner in the positions a, b, c or d by means of corresponding notches 28. Prior to the inhaling operation, the displaceable pressing-out plunger 10 must be pushed by means of the grip plate 4 over a blister cavity 31 which has not yet been emptied (not visible in FIG. 1), i.e. the pressing-out plunger 10 is positioned with the engaging function at one of the four pressing-out positions a, b, c or d. By pressing down the upper part (single lever) 2 of the housing, the blister cavity 31 located below the pressing-out plunger 10 is pressed out. In this embodiment of the inhaler, the pressing-out of a blister cavity 31 can take place not only with the index finger and thumb, but also with the whole hand, since the single lever 2 provides a broad application surface. In order to prevent slipping-off, it is additionally provided on the surface with longitudinally extending gripping grooves 35. The arcuate recess 36 in the upper part 2 of the housing and the gripping grooves 35 in the bottom part 3 of the housing facilitate the opening of the housing. In the fitted-together state, the housing is held closed by means of a pin 42 which engages in a cutout 41 in the mouthpiece 1 and the bottom part 3 of the housing. The pin 42 is attached to the upper part of the housing or single lever 2 and can be lowered in the cutout 41 when the single lever 2 is pivoted down. In order then to avoid the single lever 2 pivoting up, the mouthpiece 1, which is rotatable, is turned through about 30°. The wall of the mouthpiece 1 slides over the end of the pin 42 in such a way that the opening operation is blocked, but the single lever 2 can nevertheless be pressed downwards to press out a blister cavity 31. To open the housing, the mouthpiece 1 is turned back in the opposite direction so that the part of the cutout 41 on the mouthpiece 1 exposes the pin 42 on the single lever 2, and the single lever 2 can be pivoted upwards.

Figure 4:
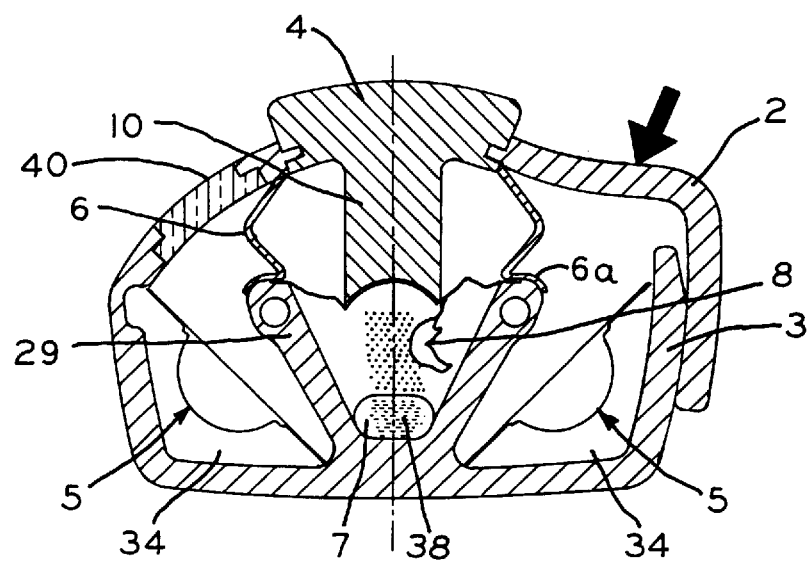
FIG. 4 shows a cross-section of the inhaler from FIG. 1 with a single lever pressed down.

The interior design of the housing can be seen in the cross-sectional illustrations of FIG. 2 to FIG. 4. Arranged in the bottom part 3 of the housing is a receiving bearing 29 for the blister strip 5, which receiving bearing comprises two longitudinally extending plates directed upwards in a V-shape. Apart from the longitudinally extending plates which can be seen in the cross-sectional drawings, the receiving bearing 29 also has two corresponding transversely extending plates on the short sides of the housing, such that the inserted blister strip 5 rests with all four sides on the bearing 29. The plates of the bearing 29 are widened slightly in the upper region in order to provide a sufficient resting surface for the blister strip 5; moreover, the plates have, at their widened upper end, an inwardly directed recess 30 of small depth, into which the blister strip 5 is inserted and which prevents the blister strip 5 from slipping inside the bearing 29. The duct 7 extending longitudinally through the housing is located in the lower region between the plates of the bearing 29 arranged in a V-shape. The duct 7 connects the mouthpiece 1, which is only visible in the perspective illustration of FIG. 1, to the air inlet opening which is not illustrated in this embodiment. The plates of the bearing 29 enclose, with the walls of the bottom part 3 of the housing, two chambers 34 which extend to the right and left next to the air duct 7 and in which blister strips 5 for later use (so-called "replacement blister strips") can be kept.

The plunger 10 with a concavely curved plunger surface 37 which is connected integrally to the grip plate 4 can be seen in FIGS. 2 to 4. The longitudinally slidable connection to the upper part 2 of the housing takes place via the grip plate 4. The part 40 of the upper part of the housing adjoining the film hinge acts as an inner or integrated lever for the plunger 10.

FIG. 2 shows the single-lever inhaler with. the housing open, i.e. the upper part 2 of the housing is pivoted upwards and the blister strip 5 can thus be placed on the bearing 29. Apart from the plunger 10, there are also two inwardly directed thin webs 6 on the single lever 2 along the long sides of the recess 27 (see FIG. 1), the web ends 6a remote from the inner surface of the upper part 2 of the housing being bent for engaging around the receiving bearing 29. There are transverse webs between the end-face ends of the webs 6. The webs 6 and the transverse webs are made of spring-elastic material so that they can be deformed (curve) when the upper part 2 of the housing is pressed down for the engagement of the plunger 10 on a blister cavity 31 and, with the spring force, press the edge of the blister strip into the bearing 29.

FIG. 3 shows the inhaler with the housing closed and a blister strip 5 inserted in the first stage of the pressing-out operation. It can be seen how the elastic webs 6 engage on the upper ends of the bearing 29 and the blister strip 5 inserted therein.

Since pressure is exerted on the single lever 2 by the user (not illustrated here) from above, the webs 6 are already under stress. The web 6 is designed in such a way that it presses all four sides of the blister strip under stress firmly onto the bearing 29 in order to fix the blister strip 5 so as to be sealed off with respect to air to a great extent. Since the plunger 10 is connected laterally to the bottom part 3 of the housing by means of an inner lever arm 40, the plunger 10 describes an arc about the pivot of the upper part 2 of the housing when the upper part of the housing is closed and, as a consequence thereof, the engagement of the edge of the curved plunger surface 37 on the outwardly curved blister cavity 31 takes place asymmetrically, i.e. in the first phase of the pressing-out operation firstly only on one side. In the stage of the pressing-out operation illustrated in FIG. 3, the upper part 2 of the housing engages slightly over the bottom part 3 of the housing.

FIG. 4 illustrates the final phase of the pressing-out operation with a blister cavity 31 which has already been opened and emptied. In comparison with FIG. 3, the webs 6 are even more stressed and the upper part 2 of the housing engages further over the bottom part 3 of the housing. The blister cavity 31 was pressed out by means of the plunger 10; the covering foil which previously sealed the blister cavity 31 is still connected to the blister strip 5 only on one side and hangs down as a tag 8, aligned parallel to the air flow, in the interior of the duct 7. The asymmetrical engagement of the plunger 10 on the blister cavity 31 caused the covering foil to tear open firstly on the side on which the curved plunger surface 37 firstly engaged. In FIG. 4, the medicament 38 drops from the opened blister cavity 31 straight into the air duct 7, from where it is made accessible to the user by means of the inhalation operation which then follows. The bold arrow in FIG. 4 is intended to show clearly at which point the application of force by the user takes place during the pressing-out operation. The lever transmission means that the effort required for pressing out the blister cavity 31 is to be less by about half than in the case of a direct pressing-out operation. When all four cavities 31 of the blister strip 5 have been emptied, the housing must be opened and a new blister strip 5 inserted.

Figure 5:
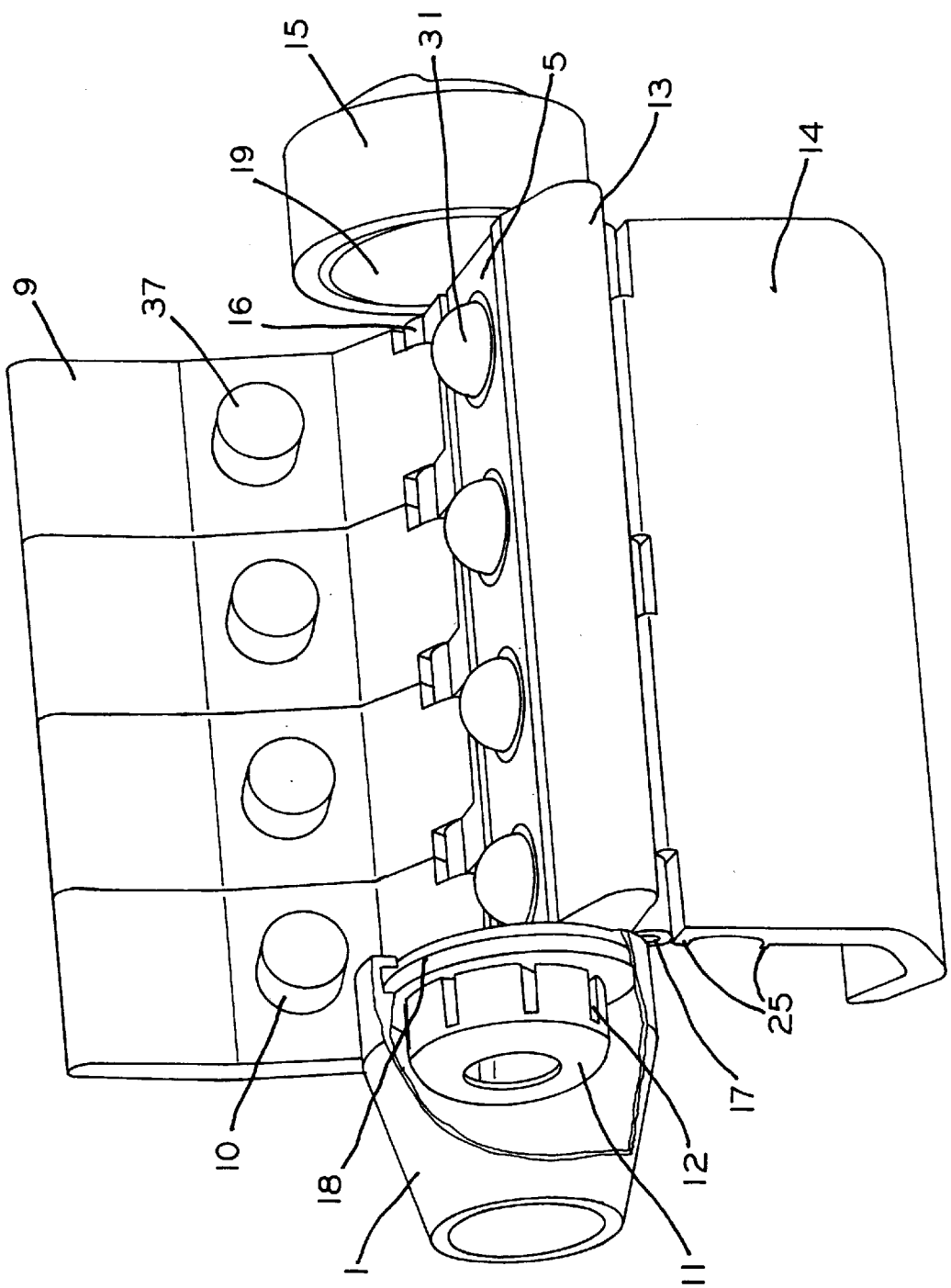
FIG. 5 shows, in a perspective illustration, an inhaler with four individual pressing-out levers pivoted open and the bottom part of the housing pivoted down.
Figure 6:
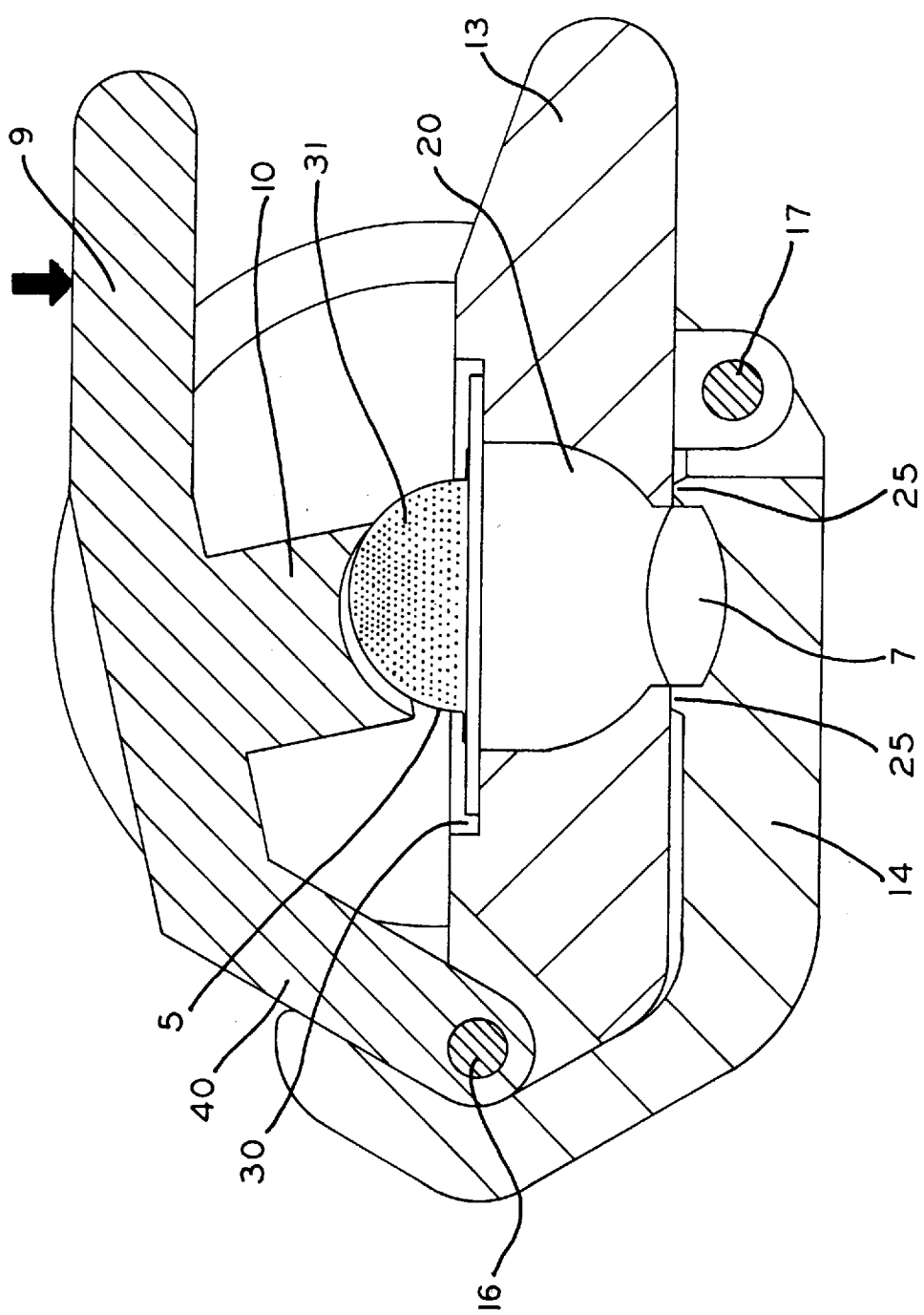
FIG. 6 shows a cross-section of the inhaler illustrated in FIG. 5 with the housing closed and a blister strip inserted.

FIGS. 5 and 6 likewise show an embodiment of the inhaler in which the pressing-out means act by means of lever arms. However, in this case, there is not just a single lever arm 2 with a displaceable pressing-out plunger 10, but there are four individual pressing-out levers 9, each having a pressing-out plunger 10, which plungers are actuated successively for pressing out the four blister cavities 31. FIG. 5 shows the four-lever inhaler with the housing pivoted open. The bottom part 14 of the housing is pivotably connected to the central part 13 of the housing by means of an appropriate hinge 17 which is attached to the long side of the central part 13. The four pressing-out levers 9 are likewise pivotably connected to the central part 13 of the housing via an appropriate hinge 16 which is located on the opposite long side of the said central part 13 of the housing.

The upper side of the central part 13 of the housing serves as a bearing for the blister strip and has, in the centre, a rectangular recess 30 for receiving the blister strip 5. Formed in the bottom of the recess 30 are four supply openings 20 which are not visible in FIG. 5 and which communicate with the air duct 7 when the housing is closed. Attached to one narrow side of the central part of the housing is a receiving plate 18 for the mouthpiece 1, and a receiving plate 19 for the end piece 15 is attached to the opposite narrow side. A cyclone chamber 11 with tangential air inlet slots 12 is formed on the receiving plate 18 for the mouthpiece 1. The mouthpiece 1, which comprises a cylindrical section and a section shaped like a truncated cone, is fastened to the receiving plate 18 and, with its cylindrical section, surrounds the cyclone chamber 11. In order to allow the entry of secondary air into the cyclone chamber 11 via the air inlet slots 12, the mouthpiece 1 has a secondary-air duct which is not illustrated here. The end piece 15 with an air inlet opening, not illustrated here, and a diaphragm valve is fastened to the receiving plate 19. The air duct 7 extends on the inner side of the pivotable bottom part 14 of the housing and is sealed off towards the side in an airtight manner only when the housing is closed by means of corresponding beads 25 extending longitudinally along the duct. When the bottom part 14 of the housing is pivoted open, the duct 7 is open and is thus easily accessible for cleaning. When the housing is closed, the duct 7 connects the air inlet opening to the mouthpiece 1 via corresponding openings in the receiving plates 18 and 19.

After the blister strip 5 has been inserted into the central part 13 of the housing, as shown in FIG. 5, the housing is pivoted closed, specifically in that firstly the four pressing-out levers 9 which in a certain way form the upper part of the housing are pivoted slightly downwards, but without already exerting pressure on the blister cavities 31 in the process, and the bottom part 14 of the housing is then pivoted upwards. FIG. 6 shows a cross-section of the four-lever inhaler pivoted closed. The end of the bottom part 14 of the housing located opposite the hinge 17 is bent over so that, in the pivoted-closed state, it engages around the pressing-out levers 9 on their lower part, and the housing remains closed by means of this engaged connection. The bottom part 14 of the housing is bent over in such a way and the pressing-out levers 9 are shaped in such a way that the plungers 10 exert slight pressure on the blister cavities 31 when the housing is closed, thus fixing them in the recess 30, but without already pressing the blister cavities 31 out. The blister strip 5 is fixed by the pressing-out levers 9 resting on it in such a way that the strip 5 cannot drop out or be removed in the closed state of the inhaler. The curvature of the bottom part 14 of the housing also means that the bottom part 14 of the housing merely needs to be pivoted upwards to close the housing, thus bringing the pressing-out levers 9 automatically into the position shown in FIG. 6. It can easily be seen in FIG. 6 how the duct 7 is sealed off laterally by the two longitudinally extending beads 25 which press against the central part 13 of the housing. If the user then wishes to inhale a dose of the medicament 38 enclosed in the blister cavities 31, he must press down one of the four pressing-out levers 9, preferably utilizing the lever transmission at the end remote from the hinge 16, the plunger 10 exerting pressure, by means of its curved plunger surface 37, on the blister cavity 31 and pressing the latter out. The bold arrow denotes such a preferred point for the application of force on the lever 9 by the user. As can be seen in FIG. 6, an asymmetrical engagement on the blister cavity 31 takes place in this embodiment too, due to the arrangement of the plunger 10 on an inner lever arm 40 connected laterally to the central part 13 of the housing, in order to tear open the covering foil 39 at one point in a targeted manner. The medicament then drops through the supply opening 20 into the duct 7 and is inhaled from there. In order to release the next dose of the medicament, a further pressing-out lever must be pressed down. Since the pressing-out levers 9 in this embodiment are considerably narrower than the single lever 2 of the embodiment described above, and since these have to be actuated individually, the pressing-out levers 9 should be pressed down by the user using one finger. Just as in the single-lever design, the effort required in this embodiment for pressing-out the blister cavities 31 is less by about half, due to the lever transmission, than in the case of a direct pressing-out operation. A particular advantage of this embodiment is the easy accessibility of the powder duct 7 and of the supply openings 20 for cleaning purposes when the housing is pivoted open.

Shown as a further embodiment in FIGS. 7 to 10 is an inhaler with pressing-out means which act directly, i.e. without lever transmissions. It can be seen in FIGS. 7 and 8 that the inhaler comprises an elongate bottom part 3 of the housing with a mouthpiece 1 and an end piece 15 and an upper part of the housing, which is described here as a housing flap 23, with integrated pressing-out plungers 10. With the housing flap 23 closed, the housing has an essentially tubular shape. The housing flap 23 is connected to the end piece 15 of the bottom part 3 of the housing via a hinge 24. Located in the housing flap 23 is a rectangular recess 22 in which four pressing-out plungers 10 are mounted withtheir grip plates 4. In the bottom part of the housing 3 there is a likewise rectangular recess 30 as a bearing for the blister strip 5. Arranged in the bottom of the recess 30 are four supply openings 20 which communicate with the powder duct 7 which is not visible in FIG. 7. The closed housing flap 23 engages in the recess 30 of the bottom part 3 of the housing and thus fixes the inserted blister strip 5. Located in the end piece 15 is the air inlet opening 32 which is provided with a diaphragm valve 21 which permits air to be sucked into the inhaler. The mouthpiece 1 has a cylindrical section and a section shaped like a truncated cone. A cyclone chamber 11 with tangential air inlet slots 12 is integrated in the cylindrical section of the mouthpiece 1. When used, the medicament 38 is flung, by the air flow sucked in through the mouthpiece, through the air duct 7 via an opening 43 onto the deflector 44. There it is disintegrated into smaller particles and then enters tangentially into the cyclone chamber 11. The secondary-air supply into the cyclone chamber 11 via the inlet slots 12 takes place via the secondary-air duct 26, visible only in the longitudinal sectional illustration of FIG. 8, which is arranged in the housing flap 23 and communicates with the interior of the mouthpiece 1.

Figure 7:
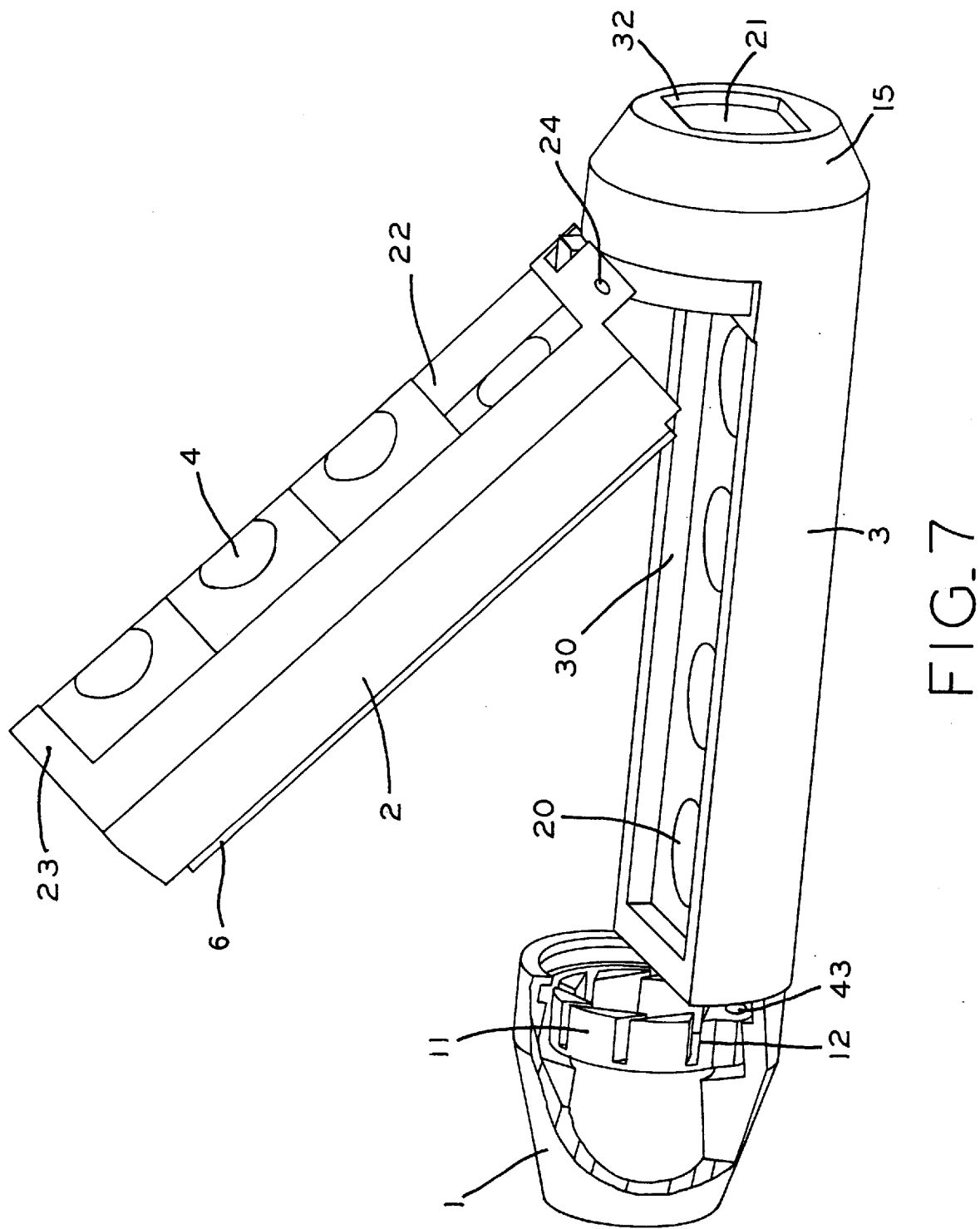
FIG. 7 shows, in a perspective illustration, an inhaler with four central pressing-out aids and the upper part of the housing pivoted open.
Figure 8:
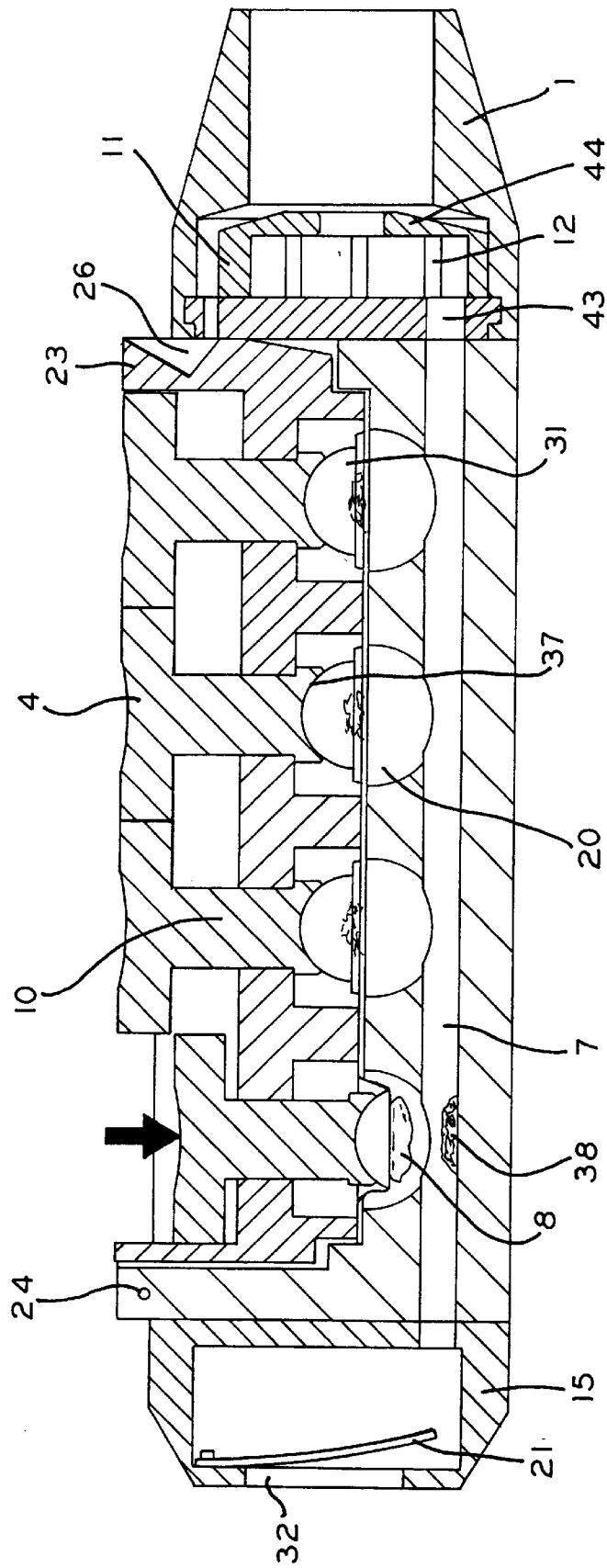
FIG. 8 shows a longitudinal section of the blister inhaler illustrated in FIG. 7 with the housing fitted together and a blister strip inserted.

While FIG. 7 shows the embodiment of the inhaler with a directly acting pressing-out device with the housing flap 23 open and a plunger 10 pressed in and no blister strip 5 inserted, the longitudinal section of FIG. 8 clearly shows the position of the blister strip in the housing and the manner of functioning of the pressing-out means. In order to empty a blister cavity 31, the user exerts pressure on one of the grip plates 4 of the pressing-out plungers 10 using one finger. By means of direct force transmission, the concavely curved plunger surface 37 engages on the blister cavity 31, the covering foil 39 tears open, and the medicament 38 drops through the supply opening 20 into the duct 7, from where it can be inhaled. The torn-open covering foil remains partially connected to the remaining covering foil 39 and hangs down as a tag 8 into the supply opening. It is not illustrated in FIG. 8 how the individual pressing-out plungers 10 with their grip plates 4 are mounted in the housing flap 23. On the one hand, there is the possibility of the pressing-out plungers 10 being arranged loosely in the housing flap 23 and only being held in the upper position when a blister strip 5 is inserted and their curved plunger surfaces 37 rest on the blister cavities 31. It is self-evident that the pressing-out plungers 10 must be so light that, when they are resting on the blister cavities 31, they do not damage the latter without the user exerting pressure on the grip plates 4. In order to avoid unintended loading of the blister cavities 31, the pressing-out plungers 10 can also be held in the upper position by means of engagement connections. When pressure is exerted by the user, these engagement connections can easily be released. A further possibility is a spring mounting of the pressing-out plungers 10.

Figure 9:
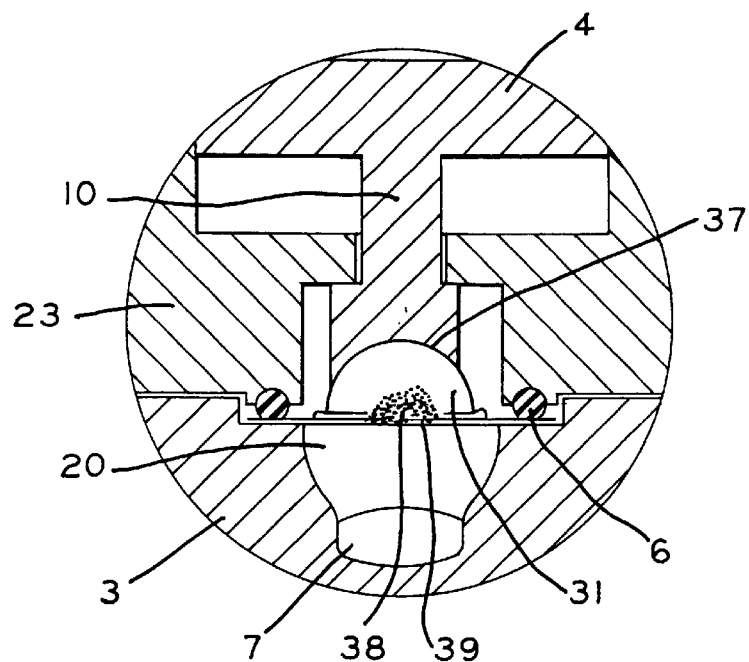
FIG. 9 shows a cross-section of the inhaler illustrated in FIG. 8.
Figure 10:
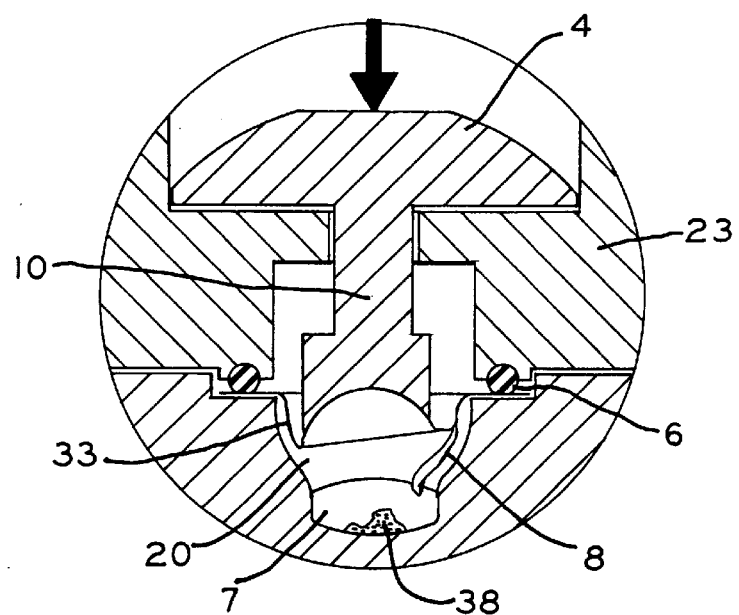
FIG. 10 shows the inhaler from FIG. 9 with a pressing-out plunger pressed down.

FIGS. 9 and 10 are cross-sectional illustrations of the inhaler according to FIGS. 7 and 8 with a pressing-out plunger 10 designed for asymmetrical engagement on the blister cavity. It cannot be seen in the longitudinal section of FIG. 8 at what angle the edge of the curved surface 37 extends relative to the longitudinal axis of the plunger 10. If the angle is not equal to 90°, the edge always intersects a plane extending perpendicular to the longitudinal axis of the housing, i.e. to the air flow, so that the cross-section of the plunger is of asymmetrical design transversely to the longitudinal axis of the housing. Only in this way is it guaranteed that the severed covering foil, the tag 8, is aligned parallel to the air flow after the pressing-out operation and does not impede the air flow. This is to be explained again with reference to FIGS. 9 and 10. FIG. 9 shows the inhaler with the housing flap 23 closed and a blister strip 5 inserted, the asymmetrical cross-section of the pressing-out plunger 10 being achieved in that the edge of the curved surface 37 of the plunger 10 extends at an angle not equal to 90° relative to the longitudinal axis of the plunger, and this plane of the edge intersects a perpendicular plane extending in the longitudinal direction of the housing. The curved surface 37 engages further around part of the corresponding surface of the blister cavity 31 than over the remaining part, such that the covering foil 39 is firstly torn open by the plunger 10 at a predetermined point. The blister strip 5 is pressed onto the bottom part 3 of the housing by the elastic webs 6 so that there is an airtight closure. The pressing-out plunger 10 is shaped asymmetrically in cross-section, so that the container film 33 is stretched to a greater extent on one side during the pressing-out operation (FIG. 10), and the covering foil 39 tears open at this point below the more greatly loaded container film 33 and remains connected to the remaining covering foil 39 on the opposite side. The medicament 38 drops through the supply opening 20 into the air duct 7. The tag 8 of the covering foil 39 hangs down, aligned parallel to the air flow, into the supply opening 20, extending right into the air duct 7.

List of reference numerals
1 Mouthpiece
2 Single lever (upper part of the housing)
3 Bottom part of the housing
4 Grip plate of the pressing-out plunger
5 Blister strip
6 Webs for pressing the blister strip on
7 Air duct
8 Tag
9 Pressing-out lever
10 Pressing-out plunger
11 Cyclone chamber
12 Tangential air inlet slots
13 Central part of the housing
14 Pivotable bottom part of the housing
15 End piece
16 Hinge of the pressing-out levers 9
17 Hinge of the pivotable bottom part 14 of the housing
18 Receiving plate for mouthpiece 1
19 Receiving plate for end piece 15
20 Supply opening
21 Diaphragm valve
22 Recess in the housing flap 23
23 Housing flap (upper part of the housing)
24 Hinge of the housing flap 23
25 Bead along the powder duct 7
26 Secondary-air duct
27 Recess in the single lever 2
28 Notches
29 Mounting for blister strip 5
30 Recess for blister strip 5
31 Blister cavity
32 Air inlet opening
33 Container film
34 Chamber for replacement blister strips
35 Gripping grooves
36 Circular-segment-shaped recess in the upper part 2 of the housing
37 Curved plunger surface
38 Medicament
39 Covering foil
40 Inner lever arm
41 Cutout in the mouthpiece 1 and bottom part 3 of the housing
42 Pin
43 Opening to the cyclone chamber 11
44 Deflector

We claim:

1. An inhaler for administering powdered medicaments from strip shaped blister packs, said blister packs each comprising a container film defining a plurality of blister cavities, one side of each said blister cavity having a generally convex outer surface, said cavities filled with powdered medicament, and a covering film for enclosing and sealing said plurality of cavities, said inhaler comprising:

an elongated housing, said housing having first and second housing members;
a hinge interconnecting said first and second housing members;
said first housing member having a support means for supporting said blister pack, said support means including a recess, said covering film directly overlaying said recess when said blister pack is supported on said support means;
a mouthpiece connected to said elongated housing;
and an air inlet opening in said elongated housing;
a duct interconnecting said mouthpiece and said air inlet opening, said recess directly opening into said duct for directly conveying the medicament from one of said blister cavities into said duct when said covering film is ruptured;
a plunger operably associated with said housing for pressing on one of said blister cavities and for rupturing said covering film to convey said medicament from said one cavity into said recess, said plunger including a concave plunger surface generally corresponding in shape to said generally convex outer surface of said blister cavities, said concave plunger surface having an edge for contacting said generally convex outer surface asymmetrically transversely to the longitudinal axis of said elongated housing whereby, upon the rupturing of said covering film, a tag is formed at the rupture in said covering film which does not impede the flow of air in said air duct.

2. An inhaler according to claim 1 wherein said mouthpiece is connected to said first housing member and said plunger includes an actuator means for depressing said plunger and for rupturing said covering film, said plunger mounted in said second housing member.

3. Inhaler according to claim 2, and including a plurality of plungers, said plungers mounted in said second housing member, each said plunger including an actuator, whereby when a blister pack is inserted into said housing and said housing is closed, each said plunger can be individually depressed onto a respective one of said blister cavities.

4. Inhaler according to claim 2, and including a plurality of plungers, each said plunger including an actuator means.

5. Inhaler according to claim 1, wherein said plunger is mounted in said second housing member, whereby, when said second housing member is depressed said plunger is actuated for pressing on and rupturing said blister cavity.

6. Inhaler according to claim 5, wherein said inhaler includes a single only plunger.

7. Inhaler according to claim 1, including a plurality of resilient inwardly directed webs connected to said second housing member for pressing said strip shaped blister pack against said support means and for orienting said blister pack in said recess when said first and second housing members are closed.

8. Inhaler according to claim 1, wherein said plunger has a longitudinal axis and wherein said concave plunger surface includes an edge which lies in a plane which extends at an angle other than 90° relative to the longitudinal axis of said plunger, the plane of said edge intersecting a perpendicular plane extending in the longitudinal direction of the housing, such that the plunger engages said generally convex outer surface of one of said blister cavities asymmetrically.

9. Inhaler according to claim 1, wherein said plunger includes a longitudinal axis and said concave plunger surface includes an edge which lies in a plane which extends at an angle of 90° relative to the longitudinal axis of said plunger, said plunger connected to said housing by a lever, said lever pivotally connected to said housing, whereby, when said lever is depressed, said plunger moves in an arc about the pivot of said lever so that said edge first contacts a side of the generally convex outer surface of one of said blister cavities.

10. Inhaler according to claim 1, wherein said mouthpiece includes a cylindrical section and a frustoconical section, said frustoconical section defining a cyclone chamber having tangential air slots and a second duct.

11. Inhaler according to claim 1, wherein said air inlet opening includes a check valve.

* * * * *